(12) United States Patent
Fountain

(10) Patent No.: US 11,298,318 B2
(45) Date of Patent: Apr. 12, 2022

(54) ONE-STEP METHOD FOR PRODUCTION OF ULTRA-SMALL LIPID STRUCTURES

(71) Applicant: FOUNTAIN TECHNOLOGIES INTERNATIONAL, LLC, Tampa, FL (US)

(72) Inventor: Michael Fountain, Tampa, FL (US)

(73) Assignee: FOUNTAIN TECHNOLOGIES INTERNATIONAL, LLC, Tampa, FL (US)

( * ) Notice: Subject to any disclaimer, the term of this patent is extended or adjusted under 35 U.S.C. 154(b) by 322 days.

(21) Appl. No.: 15/565,833

(22) PCT Filed: Apr. 13, 2016

(86) PCT No.: PCT/US2016/027194
§ 371 (c)(1),
(2) Date: Oct. 11, 2017

(87) PCT Pub. No.: WO2016/168236
PCT Pub. Date: Oct. 20, 2016

(65) Prior Publication Data
US 2018/0110732 A1    Apr. 26, 2018

Related U.S. Application Data

(60) Provisional application No. 62/146,465, filed on Apr. 13, 2015.

(51) Int. Cl.
| | |
|---|---|
| *A23L 33/10* | (2016.01) |
| *A61K 9/107* | (2006.01) |
| *A23L 27/00* | (2016.01) |
| *A23L 33/15* | (2016.01) |
| *A23L 33/16* | (2016.01) |
| *A23J 7/00* | (2006.01) |
| *A61Q 11/00* | (2006.01) |
| *A61K 8/14* | (2006.01) |
| *A23L 2/52* | (2006.01) |
| *A61K 8/34* | (2006.01) |
| *A61K 8/55* | (2006.01) |
| *A61K 8/49* | (2006.01) |
| *A23L 29/00* | (2016.01) |
| *A61K 9/127* | (2006.01) |
| *A23L 33/115* | (2016.01) |
| *A23G 1/36* | (2006.01) |
| *A61K 9/00* | (2006.01) |
| *A61K 31/353* | (2006.01) |
| *A61K 31/714* | (2006.01) |
| *A61K 33/00* | (2006.01) |
| *A61K 33/06* | (2006.01) |
| *A61K 33/14* | (2006.01) |
| *A61K 47/10* | (2017.01) |
| *A61K 47/24* | (2006.01) |
| *B01J 13/04* | (2006.01) |

(52) U.S. Cl.
CPC ............. *A61K 9/1075* (2013.01); *A23G 1/36* (2013.01); *A23J 7/00* (2013.01); *A23L 2/52* (2013.01); *A23L 27/84* (2016.08); *A23L 29/03* (2016.08); *A23L 33/10* (2016.08); *A23L 33/115* (2016.08); *A23L 33/15* (2016.08); *A23L 33/16* (2016.08); *A61K 8/14* (2013.01); *A61K 8/34* (2013.01); *A61K 8/498* (2013.01); *A61K 8/553* (2013.01); *A61K 9/0053* (2013.01); *A61K 9/107* (2013.01); *A61K 9/127* (2013.01); *A61K 9/1277* (2013.01); *A61K 31/353* (2013.01); *A61K 31/714* (2013.01); *A61K 33/00* (2013.01); *A61K 33/06* (2013.01); *A61K 33/14* (2013.01); *A61K 47/10* (2013.01); *A61K 47/24* (2013.01); *A61Q 11/00* (2013.01); *B01J 13/04* (2013.01); *A23V 2002/00* (2013.01); *A61K 9/0095* (2013.01); *A61K 2800/262* (2013.01); *A61K 2800/413* (2013.01)

(58) Field of Classification Search
None
See application file for complete search history.

(56) References Cited

U.S. PATENT DOCUMENTS

| | | | |
|---|---|---|---|
| 4,731,210 A | 3/1988 | Weder et al. | |
| 5,004,611 A | 4/1991 | Leigh | |
| 5,879,703 A | 3/1999 | Fountain | |
| 5,922,350 A | 7/1999 | Janoff et al. | |
| 8,545,874 B2 | 10/2013 | Fountain | |
| 2001/0006643 A1* | 7/2001 | Hope | .................. A61K 9/1278 424/400 |
| 2007/0154539 A1* | 7/2007 | Fountain | .............. A61K 9/0014 424/450 |

(Continued)

FOREIGN PATENT DOCUMENTS

WO    WO89/11850    12/1989

OTHER PUBLICATIONS

International Search Report, dated Aug. 8, 2016.

*Primary Examiner* — David J Blanchard
*Assistant Examiner* — Daniel F Coughlin
(74) *Attorney, Agent, or Firm* — Terry M. Sanks, Esq.; Beusse Sanks, PLLC

(57) ABSTRACT

Ultra-small Lipid Structures (USLS) with an average mean particle diameter of less than 100 nm are made using a single step process by diluting a hydro-organic solution containing lipids and passenger compounds. These particles are capable of sequestering the passenger molecules and self-assemble in a single process step into USLS. The USLS have applications in, for example, agricultural, cosmetics, pharmaceutical and food and beverage industries.

30 Claims, 4 Drawing Sheets

(56) References Cited

U.S. PATENT DOCUMENTS

| | | |
|---|---|---|
| 2008/0020124 A1* | 1/2008 | Kawashima .............. A23J 7/00 |
| | | 426/648 |
| 2010/0173014 A1 | 7/2010 | Fountain |
| 2011/0212167 A1* | 9/2011 | Ali ....................... A61K 9/0014 |
| | | 424/450 |
| 2014/0205657 A1 | 7/2014 | Mundus et al. |
| 2014/0271782 A1 | 9/2014 | Fountain |
| 2014/0335166 A1 | 11/2014 | Fountain |
| 2015/0087582 A1* | 3/2015 | LoVetri ................ A61K 31/315 |
| | | 514/2.5 |

* cited by examiner

ONE-STEP METHOD FOR PRODUCTION OF ULTRA-SMALL LIPID STRUCTURES

CROSS-REFERENCE TO RELATED APPLICATIONS

This application claims benefit of U.S. Provisional Application No. 62/146,465 filed on Apr. 13, 2015, the entire contents of which are hereby incorporated by reference as if fully set forth herein, under 35 U.S.C. § 119(e).

BACKGROUND

This invention relates to efficient methods for the production of ultra-small lipid structures (USLS; less than 100 nm in diameter, average), useful for the sequestration of passenger molecules, in a single process step.

Very small lipid particles, vesicles and other structures per se are known in the art. These structures, used for encapsulating or sequestering material for delivery in a variety of applications, are liposomes, usually comprising a lipid mono-layer or bi-layer surrounding an aqueous or semi-aqueous center, in which a compound can be dissolved or suspended for sequestration in the structure. These types of structures are useful to solubilize compounds not otherwise soluble in an aqueous solvent, to conveniently package compounds for inclusion in pharmaceuticals, foods and beverages, to mask unpleasant tastes, to produce separation of ingredients in a product, to achieve a delayed or extended release of the sequestered contents, and the like.

Previously, loaded lipid structures of a small size, i.e., less than about 200 nm, have been produced using a multi-step process. One method involved dissolving bi-layer-forming lipids in an organic solvent, drying, adding an aqueous solution that contains the dissolved passenger compound to form a thin film, and then to produce the liposomes. This process, however, generally results in structures that are too large for the most advantageous uses.

A second method involves solvent dilution. Lipids, for example soy phosphatides, are dissolved in ethanol. Water then is added, then more ethanol. This material then is placed in an aqueous environment that contains the intended passenger compound to produce liposomes of about 400-500 nm. Smaller structures have been produced according to the methods described, for example, in U.S. Pat. Nos. 5,879,703, 5,922,350, 8,545,874, 8,545,875 and 8,597,678. These methods involve producing a precursor solution of some type by adding solvents to dilute in multiple steps and then adding a solution of the passenger compound for sequestration to form the lipid structure.

Previous methods for producing and loading lipid vesicles thus involve multiple steps and produce uneven results. Therefore, there is a need in the art for an efficient method to produce loaded very small lipid structures which are shelf-stable and attractive to consumers. Preferably, such particles would be of less than 100 nm in diameter.

BRIEF DESCRIPTION

Therefore, the invention described herein includes methods of making ultra-small lipid structures and the structures, solutions for making the structures and products containing the structures.

Embodiments of the invention include a method of making ultra-small lipid structures USLS comprising the single step of diluting a stock solution containing (a) a hydro-organic solvent mixture containing about 0.1% to about 20% water and about 80% to about 99.9% of one or more water-miscible organic solvents; (b) about 50 mg/ml to about 250 mg/ml of one or more lipid compounds; and (c) one or more passenger compounds; with water at a dilution ratio of about 1:5 to about 1:200. In certain embodiments, this stock solution further comprises one or more sugars. The methods of the invention, in certain embodiments further comprise dehydrating the USLS and/or rehydrating the USLS.

In preferred embodiments, the hydro-organic solvent mixture contains about 10% water. In additional preferred embodiments, the water-miscible organic solvent is selected from the group consisting of ethanol, propanol, butanol, isopropanol, chloroform, acetone, methylene chloride and propyl glycol, and most preferably is ethanol.

In certain preferred embodiments of the invention, the stock solution contains about 20 mg/ml lipid compound. Preferably, the one or more lipid compounds are mixed phospholipids derived from plant sources containing linolenic acid and linoleic acid as the acyl chains of the phospholipids. Most preferably, the one or more lipid compounds comprise soy phospholipids.

In certain preferred embodiments, the one or more passenger compounds are hydrophilic, lipophilic, amphipathic or a combination of one or more of hydrophilic, lipophilic, or amphipathic compounds. The passenger compounds can comprise a medicament, a nutritional substance, and/or a food component.

In preferred embodiments of the invention, the dilution ratio is about 1:10 to about 1:100. In other preferred embodiments of the invention, the method has a rate of sequestration of the passenger compounds of at least 80%.

The invention also includes, in certain embodiments, ultra-small lipid structures (USLS) produced by any of the methods described herein. Preferably, these USLS have an average diameter of 100 nm or less. The USLS preferably are shelf stable, and optionally are taste-masking.

Embodiments of the invention also include an optically clear stock solution for producing ultra-small lipid structures (USLS), which comprises (a) a hydro-organic solvent mixture containing about 0.1% to about 20% water and about 80% to about 99.9% of one or more water-miscible organic solvents; (b) about 50 mg/ml to about 250 mg/ml of one or more lipid compounds; and (c) one or more passenger compounds, wherein dilution of the stock solution with water at a ratio of about 1:5 to about 1:200 produces the USLS as described herein. This stock solution preferably is shelf stable.

Additional embodiments include products containing the USLS, including, but not limited to a food product comprising the USLS, which optionally is chocolate, a medicinal product comprising the USLS, which optionally alters absorption and biodistribution of the one or more passenger compounds compared to products carrying the same passenger compounds but lacking USLS and may be formulated for oral administration, transmucosal administration, or intranasal administration. In other embodiments, the product is an oral care product comprising the USLS, which can be a liquid mouth rinse, a gel, a chewing gum, or a dissolvable strip.

BRIEF DESCRIPTION OF THE DRAWINGS

A more particular description briefly stated above will be rendered by reference to specific embodiments thereof that are illustrated in the appended drawings. Understanding that these drawings depict only typical embodiments and are not therefore to be considered to be limiting of its scope, the embodiments will be described and explained with additional specificity and detail through the use of the accompanying drawings in which.

DETAILED DESCRIPTION

Figure 1:
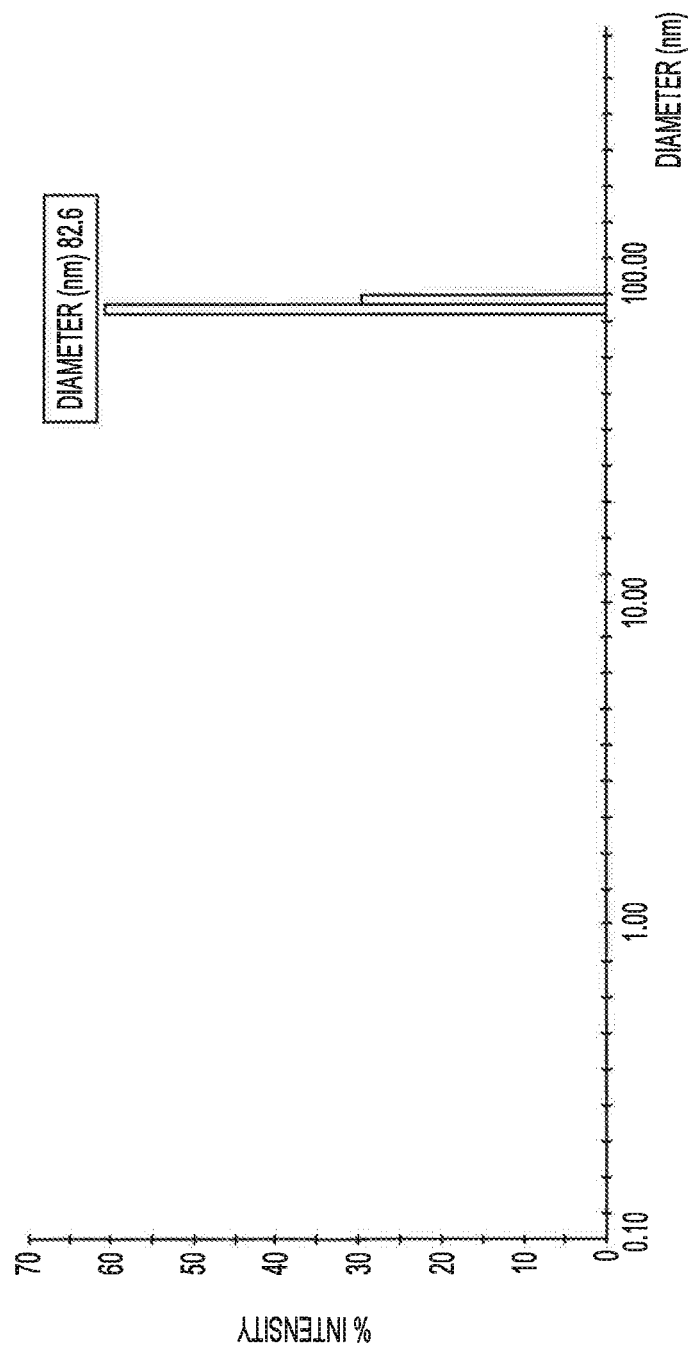
FIG. 1 is a graph of the dynamic light scattering results of the emulsion prepared in Example 1, showing the size and size distribution of the USLS.

In this specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense. The method for producing ultra-small lipid particles as described herein is a simplified process which produces particles with a narrow size range, under 100 nm, containing the sequestered material, in one step. In some embodiments, this process produces a final product that contains, in addition to the main population of USLS, a population of extremely small particles, about 1-5 nm.

The following terms as used herein have the following definitions. Where not specified, terms used herein have the meanings attributed to them in normal use by person of skill in the relevant art.

A "lipid," as the term is used herein, is any of the naturally-occurring or synthetic substances such as waxes, fats and oils that dissolve in alcohol or organic solvents generally, but not in pure water. Lipids include, but are not limited to, fatty acids, neutral fats, waxes, steroids, as well as compound lipids such as phospholipids and glycolipids. For example, mono-, di-, and tri-glycerides, cholesterol, and the like also are included. Combinations and mixtures of such compounds are included in the definition of lipids. Preferably, any of such molecules that are lipophilic or amphipathic and that can form vesicular structures (unilamellar or bilamellar) or membranes in an aqueous environment are included in this term. Phospholipids, polar lipids, sterols, sterol esters, neutral lipids, fatty acids, or any other such material or mixture of materials can be used and is contemplated for the invention. "Lipids" as used with and in the preferred inventive embodiments preferably and conveniently can be phospholipids, such as soy phospholipids.

The term "medicament," as used herein, refers to any pharmaceutical, nutraceutical, or biological compound for use in treatment of disease, or injury in human medicine or veterinary medicine, and is broadly inclusive. Examples include, but are not limited to drugs, antiseptics, analgesics, antimicrobials, or any pharmaceutical, and the like.

The term "nutritional substance," as used herein, refers to any compound with nutritive value, including macronutrients and micronutrients, such as vitamins, minerals, salts, plant extracts and the like.

The terms "particle," "structure," "liposome," and "vesicle," as used herein in the context of the invention are synonymous and refer to the ultra-small lipid structures (USLS) produced by the methods described below. The USLS are closed lipid structures composed of lipids, e.g., phospholipids, with or without lipophilic or amphipathic passenger molecules, and which are capable of sequestering an aqueous or semi-aqueous liquid, which liquid also can contain a dissolved passenger compound or material.

A "passenger" or "sequestered" compound, molecule, or material, as these terms are used herein, is any compound or group of compounds which is contained within a USLS, either in the aqueous core or within the lipid layer of the structure, or dissolved in the stock solution for producing these USLS as described below.

The term "shelf stable," as used herein, means that the product can sequester compounds for a period of at least one year and preferably for at least two years. This term is relative, and will depend at least to some extent on the stability of the passenger molecules in the product.

The term "ultra-small lipid structure (USLS)," as used herein, refers to lipid vesicles having a bilayer or non-bilayer lipid surrounding structure and an aqueous core, with an average diameter of 100 nm or less.

The particles according to embodiments of the invention are produced using a simple, one-step method in which a hydro-alcoholic solution of dissolved lipids is added to an aqueous solution of the passenger compound(s). Sub-two hundred nanometer diameter, sub-one hundred fifty nanometer diameter, or sub-one hundred nanometer diameter structures, with a narrow size range, can be formed with near 100% encapsulation of the aqueous passenger material.

The USLS according to the invention are lipid structures of less than about 150 nm average diameter, and preferably of less than about 100 nm average diameter. These structures have an outer lipid layer, which can be non-bilayer or bilayer, depending on the size of the finished particle, with an internal aqueous or semi-aqueous core. Below 40 nm, the structures will be predominately non-bilayer. Preferably, the structures contain one or more passenger compounds in the central aqueous core, in the lipid layer structure, or both. These structures are produced in a single dilution process step by mixing water with a stock hydro-organic solution containing lipid material which will form the outer lipid layer of the structure and the passenger molecules to be sequestered in the structure, once formed.

Sequestration rates of about 80% to about 95% can be achieved using methods according to embodiments of the invention. Preferably, the passenger compound(s) are sequestered at a rate of at least 80% and most preferably at least 90%.

The stock mixture containing lipid material and the passenger compound(s) in a hydro-organic solvent is an optically clear solution which is stable at room temperature. This solution can be stored indefinitely for later use or for up to 2 years.

The USLS can be surrounded by a bilayer or a non-bilayer lipid layer. The structure of the lipids in the final USLS product depends on the choice of lipids and other components to be used to form the USLS stock solution. For example, the USLS will retain, in the final formed structure, a portion of the hydro-organic stock solution used to form them. Therefore, the selection of the organic solvent can influence the final structure of the USLS significantly, and help to determine whether it is bilayer or non-bilayer in structure. Smaller molecular weight organic solvents and those with higher polarity will favor the formation of closed ultra-small bilayer structures which contain lipids, hydro-organic solution and sequestered passenger molecules. If a structure with a more negatively charged surface is desired, an additional phospholipid species, such as phosphatidic acid, can be added; to produce a more positively charged surface, an additional phospholipid species, such as phosphatidylserine can be added.

The USLS products made according to the invention optionally also contain a population of about 1% to 2% very small (1 nm-5 nm) particles, by which the product can be recognized as a form of fingerprint. These particles are non-bilayer, and due to their extremely small size may not be micellar. Without wishing to be bound by theory, these particles may be small assemblies of phospholipids bound at the polar head groups by water and ethanol.

Lipids

Lipids preferred for use with the invention include phospholipids, such as mixed natural phospholipids predominately comprising phosphatidylcholine, containing linolenic acid and linoleic acid as constituents of the acyl chains of the phospholipids. These can be found in soy, rapeseed, sunflower, poultry egg yolk, fish eggs, and bovine milk as known in the art and can be purified from these sources according to well-known methods.

In some embodiments of the invention, it is convenient to select a commercial preparation of phospholipids. A preparation comprising about 75-97% mixed soy phosphatides, for example, can be used. Commercial preparations containing 75%-80% mixed soy phosphatides, the remaining percentage being soy oils, or containing 95%-97% mixed soy phosphatides, the remaining percentage being soy oils, are available and can be used with the invention. Suitable commercial preparations having these characteristics are sold under the trade designations Alcolec S™, Alcolec X-tra A™ and Alcolec LKE™.

The concentration of the lipid layer-forming lipid or lipid mixture in the hydro-organic solvent (stock solution) varies, but cannot exceed the limitations of the solubility of the lipid or lipid mixture in the chosen hydro-organic solution. The concentration of the passenger molecule(s) to be sequestered also can vary, but cannot exceed their co-solubility with the lipid material in the hydro-organic solvent or the ability (based upon the individual passenger molecules' physical and chemical characteristics) to sequester in the USLS.

Preferably, the lipids are dissolved in a hydro-organic solvent system (see below) in a concentration range from about 50 mg/ml to about 250 mg/ml, preferably about 100 mg/ml to about 200 mg/ml, and most preferably about 150 mg/ml. Exemplary concentrations include, but are not limited to about 50 mg/ml, about 100 mg/ml, about 150 mg/ml, about 200 mg/ml, and about 250 mg/ml.

Organic Solvents

Appropriate organic solvents generally are those which produce hydro-organic solvent mixtures in which both the lipids and the intended passenger compounds are sufficiently soluble. Generally, the most preferable solvent is a mixture of water and a low molecular weight organic solvent. Low molecular weight organic solvents such as ethanol, propanol, butanol, isopropanol, chloroform, acetone, methylene chloride or propyl glycol, and the like, or any mixture thereof, are suitable. In addition, the solvent must be appropriate for the particular intended use of the USLS, and sufficiently miscible with water. If the USLS are to be employed in vivo such as for example in an intravenous admixture, the solvent must be sufficiently non-toxic in that use and generally must be biocompatible and readily miscible with biological fluids such as blood. Thus, ethanol (reagent grade) is most preferred for this type of use. Preferably, all solvents are reagent grade.

Water

The water used in the methods according to the invention can be potable water from any source, but preferably is purified water, such as distilled or deionized water. Sterile water can be used.

Hydro-Organic Solvents

USLS are prepared by making a hydro-organic solution of lipids and the passenger compound(s) to be sequestered. Appropriate hydro-organic solvent systems contain about 0.1 to about 20% water (v/v), about 0.5 to about 15% water (v/v), about 1 to about 10% water (v/v), and most preferably about 5 to about 10% water (v/v). Exemplary amounts of water include, but are not limited to about 1% water (v/v), about 5% water (v/v), about 12% water (v/v), and about 15% water (v/v), most preferably about 10% (v/v) water. The remainder of the solvent (to make up 100%) is one or more organic solvent, such as ethanol. The most preferred solvent system is 10% water and 90% reagent grade ethanol. The water used according to the methods of the invention preferably is purified, distilled or deionized water, and can be sterile water.

Passenger Compounds

Materials suitable for sequestration in the structures of the invention include any material that can be dissolved in or suspended in the hydro-organic solution used to form the final ultra-small lipid structures. Passenger compounds for sequestration in the USLS thus can be any material capable of being physically sequestered in the USLS, either in the internal (aqueous) core or as an integral component of the external lipid shell, and can be lipophilic, hydrophilic or amphipathic.

Such materials include medicaments, pharmaceutical compounds, nutritional or nutrient compounds, cosmetics, and the like. Passenger molecules such as flavors, scents, nutrients, vitamins, minerals, salts, antimicrobials, anti-inflammatories, anti-parasitics, dyes, radiolabels, radio-opaque compounds, fluorescent compounds, immunomodulating compounds, peptides, proteins, glycoproteins, lipoproteins, hormones, neurotransmitters, tumorocidal agents, growth factors, toxins, analgesics, anesthetics, mono and polysaccharides, and narcotics are non-inclusive examples of the classes of substances which can be used. Any lipophilic, hydrophilic and amphipathic materials or combination of materials can be used, if soluble in the hydro-organic solvent system.

In the pharmaceutical, nutraceutical, or nutrition arts, the invention is advantageously used to mask the taste of ingredients that otherwise would have an unpleasant taste or can be used to achieve a delayed or extended release of the contents of the USLS. Alternatively, the USLS can be used to sequester a component that is designed to be tasted, for addition to a pharmaceutical or food product, for example. The USLS can be used to produce a delayed release of the contents, for example, to bypass the stomach and release the contents in the intestine, or to separate components of a product that can react with each other during storage.

Any pharmaceutical compound for oral delivery can be used with embodiments of the invention. For example, compounds such as antibiotics (e.g., aminoglycosides, beta-lactams, and macrolides), anesthetics (e.g., lidocaine), steroids (e.g., estrogen, progesterone, stilbestrol, testosterone, and estradiol), antifungals (e.g., griseofulvin), antigenic materials (e.g., vaccines, allergy treatments), proteins, immunomodulators, monoclonal antibodies and fragments thereof, and the like are contemplated for use. Such materials include organic chemicals, salts, peptides, proteins, carbohydrates, sugars, and the like.

Vitamins, including fat-soluble and water-soluble vitamins, such as vitamin A, B vitamins, vitamin C, vitamin D, vitamin E, vitamin K, or any combination of vitamins also are contemplated for sequestration in the structures of the invention. Salts and minerals, such as sodium, potassium, magnesium, iron, and the like also can be used with the invention.

Materials useful in the cosmetic industry, such as sunscreens, tints, colorants, scents and odorants, dyes, and the like also are contemplated.

In the food and beverage industry, materials such as caffeine, flavorings (e.g., peppermint oil), colorings, salts, carbohydrates, vitamins, proteins, plant extracts (including plant nutraceuticals), and the like are contemplated for use. Such materials can be sequestered for the purpose of taste-masking, improvement in mouth-feel, protection from oxidation, and protection from reaction with other components of the product, for example.

The passenger compound(s) are in solution in the hydro-organic stock solution, and can be present in any concentration which is soluble in the solvent mixture in the presence of the lipid component. Thus, the person of skill can determine the concentration to be used, depending on the desired final product. Ranges suitable for use with the invention include any concentration that is soluble, for example from about 0.1 mg/ml to about 10 mg/ml, or from about 10 mg/ml to about 100 mg/ml, or from about 100 mg/ml to about 300 mg/ml, or up to the maximum solubility of the substance in the hydro-organic solvent system. The amount of organic solvent also can be manipulated, if needed, to increase solubility.

Other Components

Optionally, additional components can be added to the optically clear stock solution, including, for example, sugars such as, but not limited to trehalose, sucrose, maltose and fructose. In one preferred embodiment, sugars are added to the solution, particularly when it is desired to dehydrate the final product at a later stage. In addition, after the USLS are produced, the solution in which they are contained may be changed to include these sugars, or the sugars can be added to the USLS if only external sugar is needed for the product.

Process of Making

A stock solution, as described herein, is diluted in one step at a ratio of from about 1:5 to about 1:100 with water (i.e., one part solution to about 4 parts water, to one part solution to about 99 parts water). Exemplary ratios for dilution include, but are not limited to 1:5, 1:10, 1:25, 1:50, 1:75, and 1:100. A preferred dilution is 1:10 (one part solution to 9 parts water). Upon this dilution step, the USLS (final product) are formed.

Under these conditions the finished USLS consistently exhibit a tight size distribution with an average particle diameter (measured by DLS techniques) below 100 nm (generally between 50 nm and 90 nm). The product also has a very high sequestration rate of the passenger molecules (near 1000/encapsulation, or over 80%, or over 90% encapsulation) as demonstrated by the elimination of the passenger molecules' taste in the final product. In addition, both the stock solution preparations (prior to dilution) and the finished USLS preparations after dilution are optically clear and shelf stable at room temperature. The USLS product also can exhibit the presence of a small population (about 1% to 2%) of 1-5 nm particles.

The USLS have been compared to standard commercial preparations of the same passenger molecule prepared by previously available methods. Using standard tests (particle size analysis and the ability of the preparation to mask the taste of passenger molecules effectively in human test volunteers), USLS prepared according to an embodiment of the invention were found to have successfully sequestered the molecule of interest. See the Examples.

The USLS in the final product can be evaluated by dynamic light scattering (DLS) to determine the presence, size, and size distribution of the lipid structures (USLS). Persons of skill are aware of such techniques and the commercially available instruments for analyses available for counting or measuring of particles in suspension. The Wyatt DynaPro™, for example, can be used. See the Examples.

Figure 2:
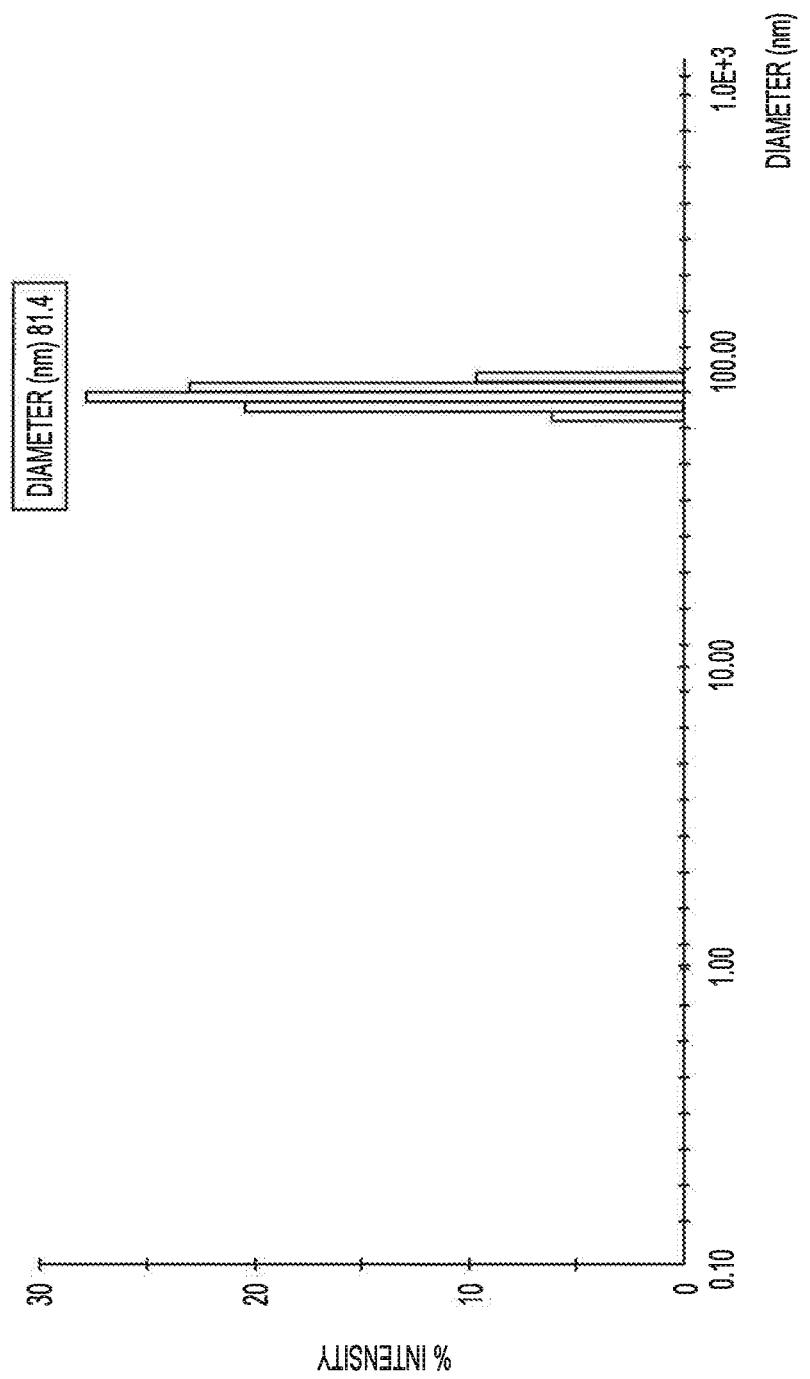
FIG. 2 is a graph showing the dynamic light scattering results of the emulsion prepared in Example 2, showing the size and size distribution of the USLS.
Figure 3:
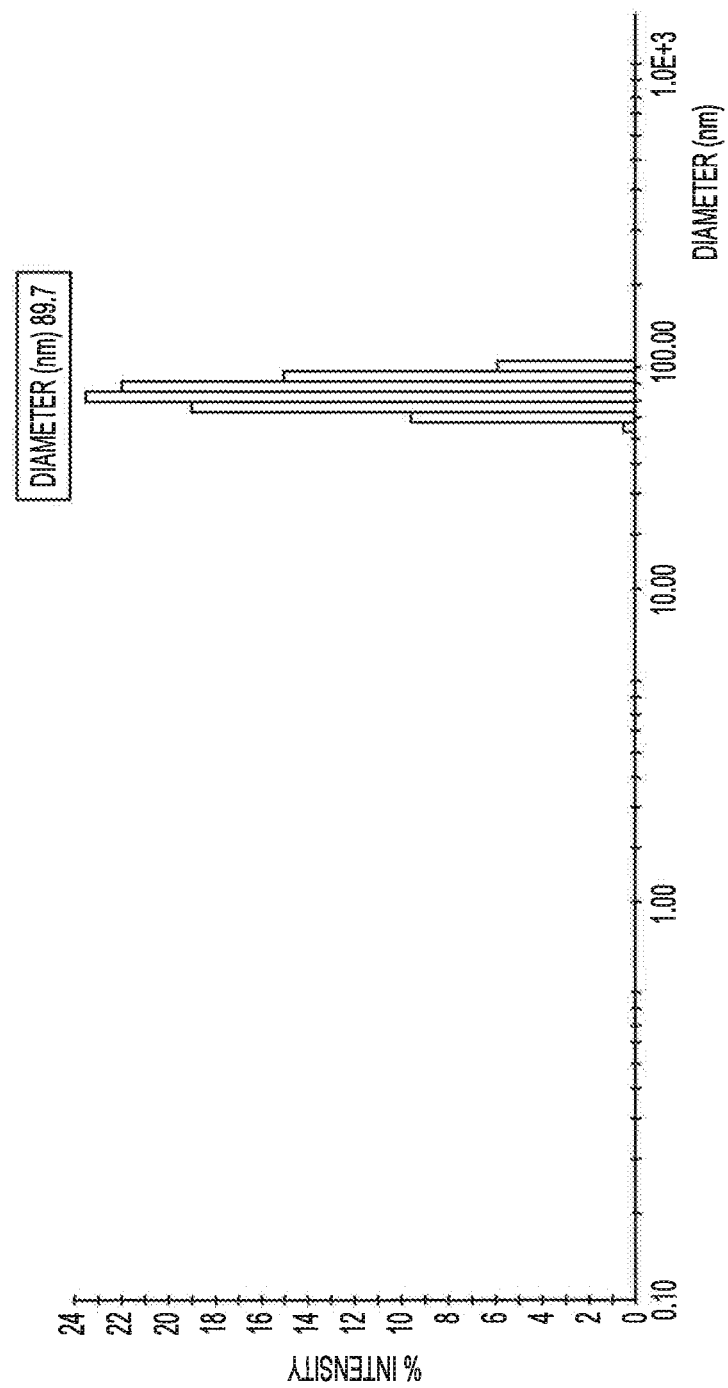
FIG. 3 is a graph showing the dynamic light scattering results of the emulsion prepared in Example 3, showing the size and size distribution of the USLS.

The inventive USLS exhibit minimal size homogeneity, as is shown by the light scattering data in FIG. 1, FIG. 2 and FIG. 3. Without wishing to be bound by theory, the size of the individual vesicles is believed to be dependent on the passenger molecule, the amphipathic materials used, and the amount of water in the hydro-organic solvent used to dissolve the lipids and passenger molecules. Increasing the amount of water may be used to increase the size of the USLS population. Increasing the concentration of a lipophilic passenger molecule increases the size of the USLS particle population if they are made using a non-bilayer-forming compound. Increasing the concentration of charged, water-soluble compounds decreases the size of the USLS population. Increasing the concentration of amphipathic passenger molecules increases the size of the USLS population.

In some embodiments of the invention, the USLS are dehydrated for storage and can be rehydrated. The USLS product preferably is dehydrated under vacuum, by freeze-drying or without freezing of the preparation. Preferably, the product is dehydrated using standard freeze-drying equipment or an equivalent apparatus, under reduced pressure or partial vacuum, as is known in the art. Optionally, the material and its surrounding medium can be frozen in liquid nitrogen prior to dehydration. Alternatively, the liposomes can also be dehydrated without prior freezing, by simply being placed under reduced pressure. Dehydration without prior freezing takes longer than dehydration with prior freezing, but the overall process is gentler without the freezing step, and thus there is in general less damage to the liposomes and a correspondingly smaller loss of the internal contents of the liposomes. For example, dehydration without prior freezing at room temperature and at a reduced pressure provided by a vacuum pump capable of producing a pressure on the order of 1 mm of mercury can take between approximately 24 and 36 hours, while dehydration with prior freezing under the same conditions can take between approximately 12 and 24 hours. In addition, spray-drying of finished USLS preparations in the presence of cryo-protective sugars can provide a dehydrated preparation of USLS suitable for rehydration at a later time.

So that the lipid structures will better survive the dehydration process without losing a substantial portion of their internal contents, one or more protective sugars can be made available to interact with the USLS and assist in keeping them intact as the water in the system is removed. A variety of sugars can be used, including such sugars as trehalose, maltose, sucrose, glucose, lactose, and dextran. In general, disaccharide sugars have been found to work better than monosaccharide sugars, with the disaccharide sugars trehalose and sucrose being most effective. Other more complicated sugars can also be used. For example, aminoglycosides, including streptomycin and dihydrostreptomycin, have been found to protect liposomes during dehydration. In certain preferred embodiments of the invention, the liposomes are dehydrated with the one or more sugars being present at both the inside and outside surfaces of the liposome membranes. In other preferred embodiments, the sugars are selected from the group consisting of trehalose, maltose, lactose, sucrose, glucose, and dextran, with the most preferred sugars from a performance point of view being trehalose and sucrose.

The one or more sugars preferably are included as part of either the internal or external media of the USLS to be dehydrated. Most preferably, the sugars are included in both the internal and external media so that they can interact with both the inside and outside surfaces of the lipid layer. Inclusion in the internal medium is accomplished by adding the sugar or sugars to the solute which the liposomes are to encapsulate. Since in most cases this solute also forms the bathing medium for the finished liposomes, inclusion of the sugars in the solute also makes them part of the external medium. Of course, if an external medium other than the original solute is used, the new external medium should include one or more of the protective sugars as well.

The amount of sugar to be used depends on the type of sugar used and the characteristics of the liposomes to be protected. Persons skilled in the art can test various sugar types and concentrations to determine which combination works best for a particular liposome preparation. See U.S. Pat. No. 5,922,350, which is hereby incorporated by reference, for exemplary methods. In general, sugar concentrations on the order of 100 mM and above have been found necessary to achieve the highest levels of protection. In terms of moles of membrane phospholipid, millimolar levels on the order of 100 mM correspond to approximately 5 moles of sugar per mole of phospholipid.

In the case of dehydration without prior freezing, if the liposomes being dehydrated are of the type which have multiple lipid layers and if the dehydration is carried out to an end point where there is sufficient water left in the preparation so that a substantial portion of the membranes retain their integrity upon rehydration, the use of one or more protective sugars may be omitted. It is preferable if the preparation contains at the end of the dehydration process at least about 2%, and most preferably between about 2% and about 5%, of the original water present in the preparation prior to dehydration.

Once liposomes have been dehydrated, they can be stored for extended periods of time until they are to be used. The appropriate temperature for storage will depend on the make-up of the liposomes and the temperature sensitivity of the encapsulated material(s). For example, as is well known in the art, various drug preparations are heat labile, and thus dehydrated liposomes containing such drugs should be stored under refrigerated conditions so that the drugs do not lose their potency. Also, for such drugs, the dehydration process is preferably carried out at reduced temperatures, rather than at room temperature.

When the dehydrated USLS are to be used, rehydration is accomplished by adding an aqueous solution, e.g., distilled water, to the dehydrated USLS and allowing them to rehydrate. The liposomes can be resuspended into the aqueous solution by gentle swirling of the solution. The rehydration can be performed at room temperature or at other temperatures appropriate to the composition of the liposomes and their internal contents. See U.S. Pat. No. 5,922,350 for suitable methods for dehydration and rehydration.

Uses

The USLS of the invention can be used in various food, cosmetic and pharmaceutical products, including liquids, solids, and vapors. The products are contemplated to be useful in forms such as gels, lotions, creams, emulsions, suspensions, freeze-dried products, spray-dried products, powders, and solutions, which can be used for topical application, oral ingestion, intravenous or other injection routes, inhalation or other administration methods and uses. The products can be incorporated into solid or liquid foods and supplement compositions for ingestion or administration. Alternatively, the USLS can be provided with a pharmaceutical or food product in a separate container, to be added by the user before use.

Specific products that advantageously can use USLS according to the invention include, but are not limited to:

1. Foods and food products, for example beverages, chocolates and other confections, chewing gums, processed foods, and the like.

2. Medicaments, medicinal products and first aid products, for example, antiseptic sprays, solid oral dosage forms, liquid oral dosage forms, rectal or vaginal suppositories, nasal sprays, inhalation or nebulizer products, transdermal patches, transmucosal dosage forms, intravenous dosage forms for dilution, intravenous forms for direct injection, subcutaneous and intramuscular depot forms, and the like for use in human or veterinary medicine.

3. Supplements, for example, rehydration products, energy drinks, vitamins, herbs, homeopathic compounds, and the like.

4. Personal Care Products, including oral care products, for example mouthwashes, mouth rinses, gels, soaps, chewing gums, dissolvable strips, throat sprays, eye drops, skin care products, creams, lotions, and the like.

5. Agricultural Products, including liquid, dried, or solid formulations for the treatment of disease in plants and animals, and the delivery of growth enhancing or protective compounds, for example.

In particular, USLS according to the invention can be used where taste-masking is desirable, for example in oral dosage forms when the active ingredient has an unpleasant flavor which might decrease compliance. A specific preferred example is a chocolate or baked good containing a marijuana component (e.g., tetrahydrocannabinol, marijuana extracts, oils and the like), where the marijuana component is sequestered in USLS. Alternatively, any plant extract, including nutraceuticals, for which taste-masking is desired, can be sequestered according to the invention. An additional preferred embodiment is a preparation of tumoricidal or other cancer chemotherapeutic medication or combination of medications sequestered in USLS.

Another application for the products in the food and beverage industry is the incorporation of substances into USLS which will be tasted, rather than masked. Flavorings such as peppermint oil and other oils can be incorporated into USLS which can be added to a base product to modify or add to the flavor thereof. This can give manufacturers and consumers options by, for example, allowing the manufacturer to produce one base flavor of a product and several different USLS-sequestered flavors, for example, or a vitamin-enrichment USLS product, which can optionally be added to the base product. Substances that are intended to be tasted can be loosely associated with the exterior of the lipid structure, while those intended to be masked can be sequestered inside the vesicle.

In pharmaceutical or nutritional products the USLS can be used to achieve a delayed release of the contents since the USLS can withstand the lower pH of the stomach and survive to be taken up from the intestine. In addition, the USLS can cross the blood-brain barrier following oral administration, and therefore can be used to administer a compound to neural tissue. In addition, USLS can be used in transmucosal administration to deliver passenger molecules into the circulatory system.

SUMMARY OF THE RESULTS

The examples below show that very small lipid vesicles, sequestering a passenger molecule, can be produced in one process step, forming USLS under 100 nm in average diameter, with consistent results and a narrow size range.

EXAMPLES

This invention is not limited to the particular processes, compositions, or methodologies described, as these may vary. The examples below therefore are intended illustrate the invention only, and to be exemplary and not limiting.

Example 1: USLS Production from Dissolved Mixtures of Phospholipids in Hydro-Organic Solution A mixture of natural soybean phospholipids (188 mg) comprising phosphatidylcholine and lysophosphatidylcholine (about 3% w/w lysophosphatidylcholine by percentage weight of total phospholipids in the mixture) was dissolved in 10 ml of a hydro-organic solvent composed of 90% ethanol and 10% distilled water (v/v). The resulting preparation was optically clear.

When subjected to dynamic light scattering analysis (DLS) using a Wyatt DynaPro™ analyzer, the product was found to have no particles above 2 nm in diameter. A population of extremely small particles was observed with an average particle diameter of approximately 1 nm (the limit of detection of the DLS analyzer). The resulting preparation was stable at room temperature and when diluted 1:75 (v/v) in distilled water produced a uniform population of USLS particles with an average diameter of less than 100 nm (average diameter of 82.6 nm). See FIG. 1. The light scattering data showed a radius of 41.3 nm. The diluted preparation also was optically clear and remained stable at room temperature.

Example 2: USLS Containing Co-Solubilized Passenger Molecules and Phospholipids in a Hydro-Organic Solution A mixture of natural soybean phospholipids (188 mg) comprising phosphatidylcholine and lysophosphatidylcholine (about 3% w/w lysophosphatidylcholine by percentage weight of total phospholipids in the mixture) was dissolved in 10 ml of a hydro-organic solvent composed of 90% ethanol and 10% distilled water (v/v). Epigallocatechin gallate (EGCG; 1,500 mg) then was dissolved in this preparation of phospholipids, ethanol and water. The resulting preparation was optically clear, ruby-red in color and stable at room temperature.

When subjected to dynamic light scattering analysis (DLS) using a Wyatt DynaPro™ analyzer, this preparation containing EGCG was found to be stable at room temperature and to contain no particles above 2 nm in diameter. A population of extremely small particles was observed with an average particle diameter of approximately 1 nm (the limit of detection of the DLS analyzer). When this lipid preparation was diluted 1:75 (v/v) with distilled water, it yielded a uniform population of USLS particles with an average diameter of less than 100 nm (average diameter 81.4 nm). See FIG. 2. The light scattering data showed a radius of 40.7 nm. This product also was optically clear and stable at room temperature.

In addition, when the product was placed on the tongue of a human volunteer, the normally bitter taste of the EGCG was masked. This test was performed as follows. Aliquots of finished USLS preparations (0.1 ml to 10 ml) were placed onto the tongue of human test volunteers, held in the oral cavity for 60 seconds while swishing in the mouth, and then expelled from the mouth. Test subjects reported their observations as to the effectiveness of masking the taste of the sequestered passenger molecule compared to an identical preparation of the passenger molecule without USLS.

Example 3: Pre-Solubilized Passenger Molecules in Hydro-Organic Solution with Subsequent Addition of Co-Solubilized Phospholipids Epigallocatechin gallate (EGCG; 1,500 mg) was dissolved in 10 ml of a hydro-organic solvent composed of 90% ethanol and 10% distilled water (v/v). A mixture of natural soybean phospholipids (188 mg) comprising phosphatidylcholine and lysophosphatidylcholine (about 3% w/w lysophosphatidylcholine by percentage weight of total phospholipids in the mixture) was dissolved in this preparation of EGCG, ethanol and water. The resulting lipid preparation was optically clear, ruby-red in color and stable at room temperature.

When subjected to dynamic light scattering analysis (DLS) using a Wyatt DynaPro™ analyzer, this preparation containing EGCG demonstrated no particles above 2 nm in diameter. A population of extremely small particles was observed with an average particle diameter of approximately 1 nm (the limit of detection of the DLS analyzer). When this lipid preparation was diluted 1:75 (v/v) with distilled water, it yielded a uniform population of USLS particles with an average diameter of less than 100 nm (average diameter 89.7 nm). See FIG. 3. The light scattering data showed a radius of 44.9 nm. The final preparation of USLS was optically clear, remaining stable at room temperature. When the product was placed on the tongue of a human volunteer as described in Example 2, the normally bitter taste of the EGCG was masked.

Example 4: USLS Containing Magnesium Gluconate

A mixture of natural soybean phospholipids (188 mg) comprising phosphatidylcholine and lysophosphatidylcholine (about 3% w/w lysophosphatidylcholine by percentage weight of total phospholipids in the mixture) was dissolved in 10 ml of a hydro-organic solvent composed of 90% ethanol and 10% distilled water (v/v). Magnesium gluconate (5.2 g) was dissolved in 150 ml distilled water. The hydro-organic solution containing soybean phosphatides was added directly to this magnesium gluconate solution. The resulting preparation was optically clear and stable at room temperature.

When subjected to dynamic light scattering analysis (DLS) using a Wyatt DynaPro™ analyzer, this preparation containing magnesium gluconate had no particles above 2 nm in diameter. A population of extremely small particles was observed with an average particle diameter of approximately 1 nm (the limit of detection of the DLS analyzer).

The preparation was stable at room temperature. When diluted 1:75 (v/v) with distilled water, the solution yielded a uniform population of USLS particles with an average diameter of less than 100 nm (average diameter 63 nm). The ultra-small particle preparation was optically clear and remained stable at room temperature. When the product was placed on the tongue of a human volunteer as described in Example 2, the flavor of the magnesium gluconate was masked.

Example 5: Preparation of Magnesium Chloride-Containing USLP

A mixture of natural soybean phospholipids (188 mg) comprising phosphatidylcholine and lysophosphatidylcholine (about 3% w/w lysophosphatidylcholine by percentage weight of total phospholipids in the mixture) was dissolved in 10 ml of a hydro-organic solvent composed of 90% ethanol and 10% distilled water (v/v). Magnesium chloride (5.2 g) was dissolved in 150 ml distilled water. The hydro-organic solution containing soybean phosphatides was added directly to this solution of magnesium chloride. The resulting preparation was optically clear and stable at room temperature.

When subjected to dynamic light scattering analysis (DLS) using a Wyatt DynaPro™ analyzer, this preparation containing magnesium chloride had no particles above 2 nm in diameter. A population of extremely small particles was observed with an average particle diameter of approximately 1 nm (the limit of detection of the DLS analyzer). The preparation was stable at room temperature. When diluted 1:75 (v/v) in distilled water, the solution produced a uniform population of USLS with an average diameter of less than 100 nm (average diameter 76 nm). The resulting final preparation was optically clear and remained stable at room temperature. When placed on the tongue of a human volunteer as described in Example 2, the taste of the magnesium chloride was masked.

Example 6: Preparation of Magnesium Lactate-Containing USLS

A mixture of natural soybean phospholipids (188 mg) comprising phosphatidylcholine and lysophosphatidylcholine (about 3% w/w lysophosphatidylcholine by percentage weight of total phospholipids in the mixture) was dissolved in 10 ml of a hydro-organic solvent composed of 90% ethanol and 10% distilled water (v/v). Magnesium lactate (5.2 g) was dissolved in 150 ml distilled water. The hydro-organic solution containing soybean phosphatides was added directly to the solution of magnesium lactate. The resulting preparation was optically clear and stable at room temperature.

When subjected to dynamic light scattering analysis (DLS) using a Wyatt DynaPro analyzer, this preparation containing magnesium lactate demonstrated no particles above 2 nm in diameter. A population of extremely small particles was observed with an average particle diameter of approximately 1 nm (the limit of detection of the DLS analyzer). The resulting preparation was stable at room temperature. When diluted 1:75 (v/v) in distilled water, the solution produced a uniform population of USLS with an average diameter of less than 100 nm (average diameter 75 nm). The resulting final preparation was optically clear and remained stable at room temperature. When placed on the tongue of a human volunteer as described in Example 2, the taste of the magnesium lactate was masked.

Example 7: Preparation of Ultra-Small Particles Containing Electrolyte Concentrate A mixture of natural soybean phospholipids (3,750 mg) comprising phosphatidylcholine and lysophosphatidylcholine (about 3% w/w lysophosphatidylcholine by percentage weight of total phospholipids in the mixture) was dissolved in 200 ml of a hydro-organic solvent composed of 90% ethanol and 10% distilled water (v/v). Sodium chloride (73 g), potassium chloride (265 g), and sodium citrate (50.5 g) were dissolved in 4800 ml distilled water. The hydro-organic solution containing soybean phosphatides was added directly to this solution of electrolyte salts. The resulting preparation was optically clear and stable at room temperature.

When subjected to dynamic light scattering analysis (DLS) using a Wyatt DynaPro™ analyzer, this preparation containing electrolyte salts was found to contain no particles above 2 nm in diameter. A population of extremely small particles was observed with an average particle diameter of approximately 1 nm (the limit of detection of the DLS analyzer). The resulting preparation was stable at room temperature. When diluted 1:75 (v/v) in distilled water, the solution produced a uniform population of USLS with an average diameter of less than 100 nm (average diameter 57 nm) with a small population of particles present in the 1 to 5 nm diameter size range. The resulting final preparation was optically clear and remained stable at room temperature. When placed on the tongue of a human volunteer as described in Example 2, the taste of the electrolyte salts was masked.

Example 8: Preparation of Vitamin B12-Containing USLS

A mixture of natural soybean phospholipids (188 mg) comprising phosphatidylcholine and lysophosphatidylcholine (about 3% w/w lysophosphatidylcholine by percentage weight of total phospholipids in the mixture) was dissolved in 10 ml of a hydro-organic solvent composed of 90% ethanol and 10% distilled water (v/v). Vitamin B12 (500 mg) was dissolved in 150 ml of distilled water. The hydro-organic solution containing soybean phosphatides was added directly to this solution of vitamin B12. The resulting preparation was optically clear and stable at room temperature.

When subjected to dynamic light scattering analysis (DLS) using a Wyatt DynaPro™ analyzer, this preparation containing vitamin B12 was found to contain no particles above 2 nm in diameter. A population of extremely small particles was observed with an average particle diameter of approximately 1 nm (the limit of detection of the DLS analyzer). The resulting preparation was stable at room temperature. When diluted 1:10 (v/v) in distilled water, the solution produced a uniform population of USLS with an average diameter of less than 100 nm (average diameter 78 nm). The resulting final preparation was optically clear and remained stable at room temperature. When placed on the tongue of a human volunteer as described in Example 2, the taste of the vitamin B12 was masked.

Figure 4:
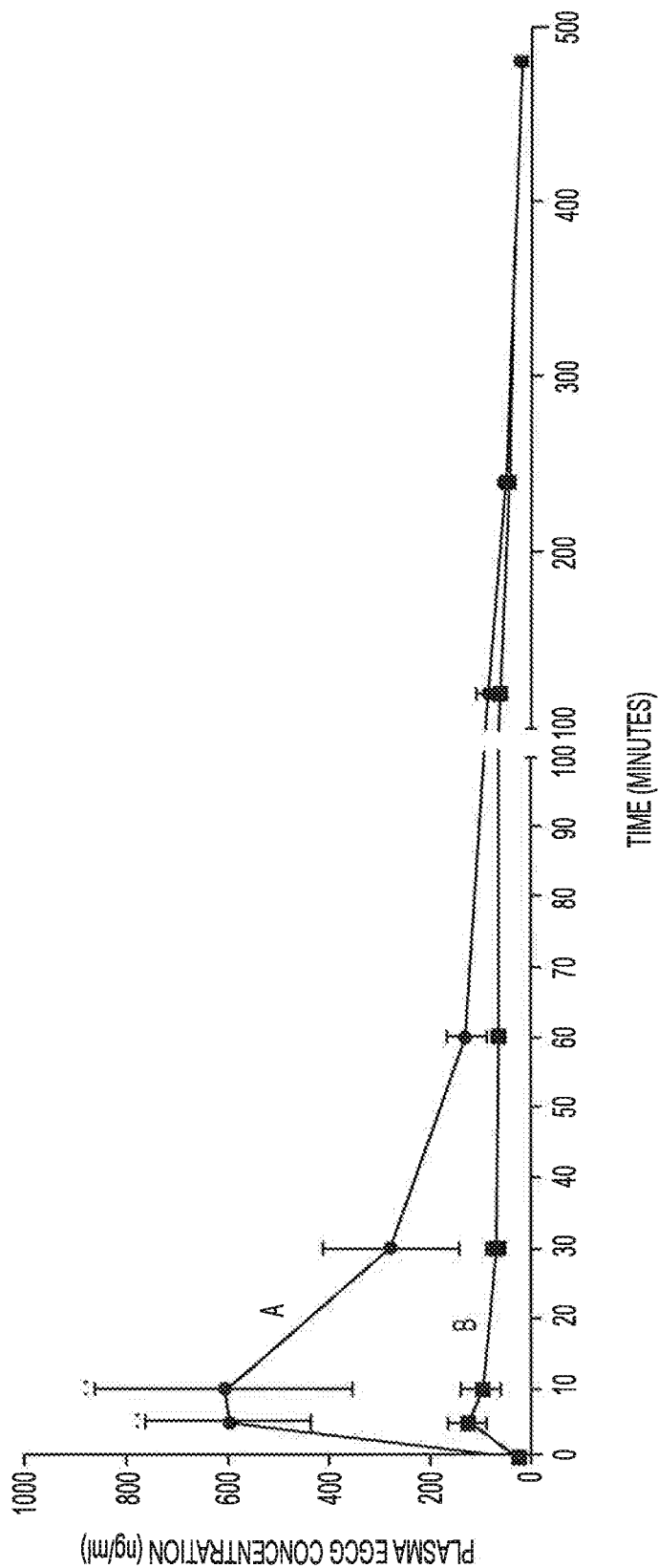
FIG. 4 is a graph showing the plasma concentrations of EGCG when administered to rats as EGCG (curve B) or as USLS containing EGCG (Example 3, curve A), by oral gavage (see Example 9).

Example 9: Pharmacokinetic Parameters of EGCG and USLS-Sequestered EGCG after Oral Administration Groups of 10 200-g male rats were administered EGCG by oral gavage, in the form of the USLS prepared as in Example 3 (2.1 ml; 100 mg/kg body weight) or as an identical preparation of EGCG without USLS. Blood samples were collected at 5, 10, 30, 60, 120, and 480 minutes post administration. See FIG. 4, which shows the mean concentration of EGCG at the indicated time points, +/−SEM, for USLS-sequestered EGCG (curve A) and EGCG without USLS (curve B). Within 5 minutes after oral administration, the USLS-sequestered compound produced a plasma concentration of 600 ng/ml and a peak plasma concentration of 605 ng/ml at 10 minutes post administration. The EGCG administered without sequestration in USLS produced a peak plasma concentration of only 150 ng/ml at 5 minutes post administration. Therefore, the USLS-sequestered product demonstrated a peak plasma concentration 4 times greater than that without USLS.

The pharmacokinetic parameters Cmax (maximum serum concentration), Tmax (time maximum serum concentration is reached), AUC (area under the curve), and Relative Bioavailability were determined from the plasma data and are presented in Table 1, below. The results demonstrated a significantly enhanced absorption of EGCG when administered in USLS compared to administration without USLS sequestration.

TABLE 1

Pharmacokinetic Data

|  | Cmax | Tmax | AUC (0-240 min) | Relative Bioavailability |
|---|---|---|---|---|
| USLS-EGCG | 704.67 | 10 | 36,529 | 2.5 |
| EGCG control | 116.57 | 5 | 14,261 | 1.0 |

REFERENCES

All publications mentioned below and throughout the application are hereby incorporated by reference in their entirety.
1. United States Patent Publication No. 2014-0271782 to Fountain
2. United States Patent Publication No. 2015-0342226 to Fountain
3. U.S. Pat. No. 4,588,578 to Fountain
4. U.S. Pat. No. 5,269,979 to Fountain
5. U.S. Pat. No. 5,879,703 to Fountain
6. U.S. Pat. No. 5,922,350 to Janoff
7. U.S. Pat. No. 8,545,874 to Fountain
8. U.S. Pat. No. 8,545,875 to Fountain
9. U.S. Pat. No. 8,597,678 to Fountain

What is claimed is:

1. A method for preparing at least one ultra-small lipid structure (USLS) comprising the step of diluting a solution, in a single dilution process step, with water at a dilution ratio of about 1:5 to about 1:200,
wherein the solution comprises:
(a) a hydro-organic solvent mixture containing about 0.1% to about 20% (v/v) water and about 80% to about 99.9% (v/v) of one or more water-miscible organic solvents;
(b) about 50 mg/ml to about 250 mg/ml of one or more lipid compounds, wherein prior to diluting the solution, none of the one or more lipid compounds in the solution have a closed lipid structure; and
(c) one or more passenger compounds, wherein the at least one ultra-small lipid structure has a closed lipid structure comprising at least one of the one or more passenger compounds sequestered therein as formed during the single dilution process step, and
wherein the term "ultra-small lipid structures (USLS)" refers to lipid vesicles having a bilayer or non-bilayer lipid surrounding structure and an aqueous or semi-aqueous core, and having an average diameter of 100 nm or less as measured using a dynamic light scattering (DLS) analyzer,
wherein the USLS product obtained contains a population of from 1% to 2% particles having diameter of from 1 nm to 5 nm as measured using a dynamic light scattering (DLS) analyzer.

2. The method of claim 1, wherein the solution further comprises one or more sugars.

3. The method of claim 1, further comprising dehydrating the at least one ultra-small lipid structure.

4. The method of claim 3, further comprising rehydrating the at least one ultra-small lipid structure.

5. The method of claim 1, wherein the hydro-organic solvent mixture contains about 10% (v/v) water.

6. The method of claim 1, wherein at least one of the one or more water-miscible organic solvents is selected from the group consisting of ethanol, propanol, butanol, isopropanol, chloroform, methanol, methylene chloride, and propyl glycol.

7. The method of claim 6, wherein the at least one of the one or more water-miscible organic solvents is ethanol.

8. The method of claim 1, wherein the comprises about 20 mg/ml lipid compound.

9. The method of claim 1, wherein at least one of the one or more lipid compounds is derived from a plant source.

10. The method of claim 1, wherein at least one of the one or more lipid compounds comprises a soy phospholipid.

11. The method of claim 1, wherein the one or more passenger compounds are hydrophilic, lipophilic, amphipathic or a combination of one or more of hydrophilic, lipophilic, or amphipathic compounds.

12. The method of claim 1, wherein the one or more passenger compounds comprise a medicament.

13. The method of claim 1, wherein the one or more passenger compounds comprise a nutritional substance.

14. The method of claim 1, wherein the one or more passenger compounds comprise a food component.

15. The method of claim 1, wherein the dilution ratio is about 1:10 to about 1:100.

16. The method of claim 1, wherein the method has a rate of sequestration of the passenger compounds of at least 80%.

17. The method of claim 1, wherein the solution is produced by mixing together each component of (a), (b), and (c) added in its entirety.

18. The method of claim 1, wherein the at least one ultra-small lipid structure has an average diameter of 100 nm or less.

19. The method of claim 1, wherein the at least one ultra-small lipid structure is taste-masking.

20. The method of claim 1, wherein the at least one ultra-small lipid structure is shelf stable.

21. The method of claim 1, further comprising including the at least one ultra-small lipid structure in a food product.

22. The method of claim 21, wherein the food product is chocolate.

23. The method of claim 1, further comprising including the-at least one ultra-small lipid structure in a medicinal product.

24. The method of claim 23, wherein the medicinal product alters absorption and biodistribution of the one or more passenger compound compared to products carrying the same passenger compounds, but lacking the at least one ultra-small lipid structure.

25. The method of claim 23, further comprising formulating the medicinal product for oral administration, transmucosal administration, or intranasal administration.

26. The method of claim 1, further comprising including the at least one ultra-small lipid structure in an oral care product.

27. The method of claim 26, further comprising formulating the oral care product as a liquid mouth rinse, a gel, a chewing gum, or a dissolvable strip.

28. A method for preparing at least one ultra-small lipid structure (USLS) comprising the step of diluting a solution, during a single step dilution process, with water at a dilution ratio of about 1:5 to about 1:200,
wherein the solution comprises:
(a) a hydro-organic solvent mixture containing about 0.1% to about 20% (v/v) water and about 80% to about 99.9% (v/v) of one or more water-miscible organic solvents;
(b) about 50 mg/ml to about 250 mg/ml of one or more lipid compounds, wherein prior to diluting the solution, none of the one or more lipid compounds in the solution have a closed lipid structure; and
(c) one or more passenger compounds,
wherein the at least one ultra-small lipid structure has a closed lipid structure comprising at least one of the one or more passenger compounds internally sequestered therein as formed during the single step dilution process, and
wherein the term "ultra-small lipid structures (USLS)" refers to lipid vesicles having a bilayer or non-bilayer lipid surrounding structure and an aqueous or semi-aqueous core, and having an average diameter of 100 nm or less as measured using a dynamic light scattering (DLS) analyzer.

29. The method of claim 1, wherein the one or more lipid compounds are mixed phospholipids derived from plant sources containing linolenic acid and linoleic acid as the acyl chains of the phospholipids;
wherein the one or more lipid compounds comprise soy phospholipids.

30. The method of claim 1, wherein the one or more passenger compounds are hydrophilic, lipophilic, amphipathic or a combination of one or more of hydrophilic, lipophilic, or amphipathic compounds; or
wherein the passenger compounds comprise a medicament; or
wherein the passenger compounds comprise a nutritional substance; or
wherein the passenger compounds comprise a food component; or
wherein the dilution ratio is about 1:10 to about 1:100; or
wherein the method has a rate of sequestration of the passenger compounds of at least 80%; or
wherein the solution is produced by mixing together each component of (a), (b), and (c) added in its entirety.

* * * * *